(12) United States Patent
Chun et al.

(10) Patent No.: US 9,776,644 B2
(45) Date of Patent: Oct. 3, 2017

(54) ON-VEHICLE SITUATION DETECTION APPARATUS AND METHOD

(71) Applicant: HYUNDAI MOBIS CO., LTD., Seoul (KR)

(72) Inventors: In-Sung Chun, Seongnam-si (KR); Jun-Han Lee, Yongin-si (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 125 days.

(21) Appl. No.: 14/656,378

(22) Filed: Mar. 12, 2015

(65) Prior Publication Data
US 2016/0009295 A1    Jan. 14, 2016

(30) Foreign Application Priority Data

Jul. 10, 2014 (KR) .................. 10-2014-0086597

(51) Int. Cl.
*B60W 50/14* (2012.01)
*B60W 50/16* (2012.01)
(Continued)

(52) U.S. Cl.
CPC .............. *B60W 50/14* (2013.01); *A61B 5/18* (2013.01); *A61B 5/6893* (2013.01); *A61B 5/7267* (2013.01); *B60C 5/005* (2013.01); *B60W 50/16* (2013.01); *G07C 5/085* (2013.01); *G07C 5/0808* (2013.01); *A61B 5/0077* (2013.01); *A61B 5/7203* (2013.01); *B60W 2050/143* (2013.01);
(Continued)

(58) Field of Classification Search
CPC ......... B60W 50/14; B60W 50/16; A61B 5/18; A61B 5/6893; A61B 5/7267; B60Q 5/005; G07C 5/0808; G07C 5/085
See application file for complete search history.

(56) References Cited

U.S. PATENT DOCUMENTS 9,096,234 B2 *   8/2015   Frye ...................... B60R 16/023
2008/0294690 A1 * 11/2008   McClellan ............ G01S 5/0027
(Continued)

FOREIGN PATENT DOCUMENTS

CN         103839379 A      6/2014
CN         104112334 A     10/2014
(Continued)

*Primary Examiner* — Thomas G Black
*Assistant Examiner* — Sze-Hon Kong
(74) *Attorney, Agent, or Firm* — Knobbe Martens Olson & Bear LLP

(57) ABSTRACT

An on-vehicle situation detection apparatus may include a detection unit to identify a driver and acquire driver status data and data about vehicle driving information or vehicle surrounding obstacles, a driving pattern learning unit to learn and store a driving pattern of a driver, based on the data acquired by the detection unit, a weighted value determination unit to determine a weighted value assigned to the information data acquired by the detection unit, based on the driving pattern learned by the driving pattern learning unit, a determination unit to determine a safe driving state of the driver, based on the data to which the weighted value determined by the weighted value determination unit is assigned, and a warning unit to warn the driver when the driver is determined to be not in the safe driving state.

10 Claims, 14 Drawing Sheets

(51) Int. Cl.
  *G07C 5/08* (2006.01)
  *B60C 5/00* (2006.01)
  *A61B 5/18* (2006.01)
  *A61B 5/00* (2006.01)

(52) U.S. Cl.
  CPC ..... *B60W 2540/22* (2013.01); *B60W 2540/28* (2013.01); *B60W 2540/30* (2013.01); *B60W 2550/10* (2013.01)

(56) References Cited

U.S. PATENT DOCUMENTS

| | | | | |
|---|---|---|---|---|
| 2009/0326774 | A1* | 12/2009 | Wang | B60T 7/22 701/70 |
| 2011/0202216 | A1* | 8/2011 | Thai-Tang | B60W 10/08 701/22 |
| 2014/0051041 | A1* | 2/2014 | Stefan | G09B 19/167 434/65 |
| 2014/0162219 | A1* | 6/2014 | Stankoulov | G09B 19/167 434/65 |
| 2014/0236386 | A1* | 8/2014 | Yoshizawa | B60W 30/08 701/1 |
| 2014/0278569 | A1* | 9/2014 | Sanchez | G06Q 40/08 705/4 |
| 2015/0002286 | A1* | 1/2015 | Kasai | B60K 35/00 340/438 |
| 2015/0009010 | A1* | 1/2015 | Biemer | G01G 19/44 340/5.83 |
| 2015/0092056 | A1* | 4/2015 | Rau | G08G 1/167 348/148 |
| 2015/0149071 | A1* | 5/2015 | Uno | G08G 1/09626 701/408 |
| 2015/0166059 | A1* | 6/2015 | Ko | B60W 30/09 701/28 |
| 2015/0213555 | A1* | 7/2015 | Barfield, Jr. | H04W 4/046 705/4 |
| 2015/0274017 | A1* | 10/2015 | Frye | B60R 16/023 701/36 |
| 2015/0294422 | A1* | 10/2015 | Carver | G07C 5/008 705/4 |

FOREIGN PATENT DOCUMENTS

| | | |
|---|---|---|
| JP | 05-162566 A | 6/1993 |
| JP | 4211831 B2 | 1/2009 |
| JP | 2013-155632 A | 8/2013 |
| JP | 5446313 B2 | 3/2014 |
| KR | 10-0282903 B1 | 3/2001 |
| KR | 10-1276770 B1 | 6/2013 |
| KR | 10-2014-0002373 A | 1/2014 |

* cited by examiner

ON-VEHICLE SITUATION DETECTION APPARATUS AND METHOD

CROSS-REFERENCE TO RELATED APPLICATIONS

This application claims priority to Korean Patent Application No. 10-2014-0086597, filed on Jul. 10, 2014, which is incorporated herein by reference in its entirety.

TECHNICAL FIELD

The present disclosure relates to an on-vehicle situation detection apparatus and method; and, particularly, to an on-vehicle situation detection apparatus and method, which generally analyze driver behavior as well as vehicle driving patterns to minimize or reduce an unexpected accident using a driver's driving load and vehicle surrounding information.

BACKGROUND

In general, vehicles offer convenience of mobility and time efficiency for persons, but require care during use because of the risk of causing serious damage to surrounding persons in addition to a driver due to carelessness of the driver. Particularly, in recent years, intelligent and enhanced vehicles have gradually increased by technological convergence of vehicles and ICT (Information & Communication Technology). Thus, safe driving assistance systems provided in the vehicles serve to recognize dangerous situations and inform a driver of the recognized situations. Korean Patent Publication No. 10-0282903 (Road Lane Departure Prevention Apparatus) discloses a safe driving assistance system.

SUMMARY

An embodiment of the present invention is directed to an on-vehicle situation detection apparatus and method, which grasp a driver's mental and physical condition to determine whether or not a driver drives a vehicle with safety and induce the driver to drive the vehicle with safety in various ways when the driver is determined to be not in a safe driving state so as to protect the driver. Another embodiment of the present invention is directed to an on-vehicle situation detection apparatus and method, which detect situations in real time through rapid calculation since a considerable time is required when a great deal of data is collected from a plurality of sensors and the situations are detected according to technological development. Another embodiment of the present invention is directed to an on-vehicle situation detection apparatus and method, which examine a determination result for error removal such that the determination result is accurate in order to detect a driver situation and induce safe driving.

Other aspects and advantages of the present invention can be understood by the following description, and become apparent with reference to the embodiments of the present invention. Also, it is obvious to those skilled in the art to which the present invention pertains that the aspects and advantages of the present invention can be realized by the means as claimed and combinations thereof.

One aspect of the invention provides a method of assessing safety of driving a vehicle is provided. The method comprises: identifying a driver who drives a vehicle; retrieving the recorded driving pattern of the driver from a memory; acquiring data from a plurality of sensors mounted on the vehicle while the driver is driving so as to get current driving pattern of the driver; quantifying differences between the recorded driving pattern and the current driving pattern into a value; determining whether the value is within a predetermined range. When determined that the value is not within a predetermined range, a warning is provided to the driver. When determined that the value is within a predetermined range, the current driving pattern is processed and saved to update the recorded driving pattern of the driver.

In accordance with an embodiment of the present invention, an on-vehicle situation detection apparatus includes a detection unit (10) to identify a driver and acquire driver status data, vehicle driving information data and vehicle surrounding obstacle data, a driving pattern learning unit (20) to learn and store a driving pattern of a driver, based on the data acquired by the detection unit (10), a weighted value determination unit (30) to determine a weighted value assigned to the information data acquired by the detection unit (10), based on the driving pattern learned by the driving pattern learning unit (20), a determination unit (40) to determine a safe driving state of the driver, based on the data to which the weighted value determined by the weighted value determination unit (30) is assigned, and a warning unit (50) to warn the driver when the driving state of the driver is determined to be not in the safe driving state by the determination unit (40).

The on-vehicle situation detection apparatus may further include a memory unit (60) for storing the data.

The detection unit (10) may include a driver status detection section (11) which includes one or more of an infrared LED imaging device, a steering wheel speed detection sensor, a steering wheel angle detection sensor, a suspension movement detection sensor, a pedal operation detection sensor, a multifunctional switch operation detection sensor, a voice recognition sensor, an AVN (Audio Video Navigation) operation detection sensor, an air conditioning device operation detection sensor, a gearbox sensor, a console box operation detection sensor, and a glove box operation detection sensor, and a vehicle surrounding situation detection section (12) which includes one or more of an SCC (Smart Cruise Control), an LKAS (Lane Keeping Assistant System), an SPAS (Smart Parking Assistant System), an AVM (Around View Monitoring), a camera, and a radar.

The determination unit (40) may include a calculation learning unit (70) to arrange the data, to which the weighted value determined by the weighted value determination unit (30) is assigned, in the order of data causing an integrated risk index to exceed a preset reference risk index and to select only a plurality of high data, a calculation unit (80) to calculate a driver's integrated risk index by adding up respective risk indexes which multiply the data selected by the calculation learning unit (70) by a weighted value for each data assigned by the weighted value determination unit, an examination unit (90) to determine whether a calculated result in the calculation unit (80) is valid, and a control unit (100) to determine whether the integrated risk index exceeds a preset reference risk index when the calculated result is determined to be valid in the examination unit (90).

The warning unit (50) may include one or more of a warning sound output device (51), a driving load display device (52), and a vehicle control device (53).

In accordance with another embodiment of the present invention, an on-vehicle situation detection method includes performing driver recognition (S100) of calling pre-stored driver information to compare whether the driver information coincides with a current driver, performing driving pattern calling (S200) of calling a pre-stored driving pattern of the driver identified by the performing driver identification (S100) from a memory unit (60), performing detection (S300) of collecting driver status information and vehicle driving information or vehicle surrounding obstacle information, performing driving pattern learning (S400) of learning the pre-stored driving pattern called by the performing driving pattern calling (S200) and a driving pattern derived from the performing detection (S300) to store the learned driving pattern in the memory unit (60), performing weighted value determination (S500) of determining a weighted value assigned to each data acquired from the performing detection (S300), based on the driving pattern learned in the performing driving pattern learning (S400), performing determination (S600) of determining a safe driving state of the driver, based on the data to which the weighted value determined in the performing weighted value determination (S500) is assigned, and performing warning (S700) of warning the driver when the driver is determined to be not in the safe driving state in the performing determination (S600).

The performing driver recognition (S100) may include performing driver data acquisition (S110) of acquiring image data of pupils or faces through an imaging device, and performing driver identification (S120) of comparing the image data of pupils and faces acquired by the performing driver data acquisition (S110) with the pre-stored driver information in the memory unit (60) to identify the driver.

The performing driving pattern calling (S200) may call a pre-stored default driving pattern when a driver coinciding with the pre-stored driver information in the performing driver recognition (S100) is not present.

The performing detection (S300) may include performing driver status detection (S310) of detecting one or more of a driver eyelid, a driver pupils, a steering wheel speed, a steering wheel angle, a suspension movement, whether or not an accelerator pedal is operated, whether or not a brake pedal is operated, whether or not a multifunctional switch is operated, whether or not a driver makes conversation, whether or not an AVN is operated, whether or not an air conditioning device is operated, whether or not a gearbox is operated, whether or not a console box is operated, and whether or not a glove box is operated, and performing vehicle surrounding situation detection (S320) of detecting a vehicle surrounding situation using one or more of an SCC (Smart Cruise Control), an LKAS (Lane Keeping Assistant System), an SPAS (Smart Parking Assistant System), an AVM (Around View Monitoring), a camera, and a radar.

The performing driving pattern learning (S400) may include performing driving pattern comparison (S410) of comparing the pre-stored driving pattern of the driver called by the performing driving pattern calling (S200) with a current driving pattern by the data acquired from the performing detection (S300), performing driving pattern determination (S420) of determining whether a difference of both in the performing driving pattern comparison (S410) is within a preset noise range, performing driving pattern storage (S430) of learning a current driving pattern when the difference of both is equal to or less than the preset noise range in the performing driving pattern determination (S420) to store the learned driving pattern in the memory unit (60), and performing noise removal (S440) of excluding a current driving pattern from a subject to be learned when the difference of both exceeds the preset noise range in the performing driving pattern determination (S420).

The performing weighted value determination (S500) may assign a weighted value determined according to affecting a driver's integrated risk index to the data acquired by the performing detection (S300).

The performing weighted value determination (S500) may compare the acquired information data and the calculated integrated risk index with an information data reference value and an integrated risk index reference value to change a weighting, by feedback of a result from the performing warning (S700).

The performing weighted value determination (S500) may change a weighted value according to the following equation:

$$\alpha(n+1)=\alpha(n), \text{ if } W<d_W \text{ and } R\geq d_R$$

$$\alpha(n+1)=\alpha(n)+\delta, \text{ if } W\geq d_W$$

$$\alpha(n+1)=\alpha(n)-\delta, \text{ if } W<d_W \text{ and } R<d_R,$$

where $R$=integrated risk index,
$\alpha$=weighting,
$\alpha(n+1)$=weighted value changed by feedback,
$\alpha(n)$=weighted value before change,
$W$=acquired information data,
$d_R$=integrated risk index reference value,
$d_W$=information data reference value, and
$\delta=\alpha(n)/R$.

The performing determination (S600) may include performing calculation learning (S610) of arranging a great deal of data, to which the weighted value determined in the performing weighted value determination (S500) is assigned, in the order of data causing an integrated risk index to exceed a preset reference risk index and of selecting only a plurality of high data.

The performing determination (S600) may include performing calculation (S620) of calculating a driver's integrated risk index by adding up respective risk indexes which multiply the data selected in the performing calculation learning (S610) among the data, to which the weighted value determined in the performing weighted value determination (S500) is assign, by a weighted value for each data assigned in the performing weighted value determination (S500).

The performing determination (S600) may include performing examination (S630) of comparing the integrated risk index calculated by the performing calculation (S620) with an examination risk index calculated based on the pre-stored driving pattern to determine whether a difference of both indexes is within a preset error range.

The performing determination (S600) may include performing control (S640) of comparing the integrated risk index with a preset reference risk index when the difference between the integrated risk index and the examination risk index is determined to be within the preset error range in the performing examination (S630), to determine whether or not to inform of warning.

The performing warning (S700) may include performing first warning (S710) of executing one or more of warning sound generation through a speaker (S711), warning display through an AVN or a HUD (S712), and vibration notification through vibration of a steering wheel or a seat (S713) when an integrated risk index is equal to or greater than a preset first reference risk index and is less than a preset second reference risk index, performing second warning (S720) of holding functions of the AVN when the integrated risk index is equal to or greater than a preset second reference risk index and is less than a preset third reference risk index, performing third warning (S730) of forcibly stopping a vehicle when the integrated risk index is equal to or greater than a preset third reference risk index, and performing information transfer (S740) of transferring information to the performing weighted value determining (S500) for change of the weighted value through feedback.

DETAILED DESCRIPTION

Embodiments of the present invention will be described below in more detail with reference to the accompanying drawings.

Generally, a safe driving assistance system mainly recognizes dangerous situations by collecting information through external sensors (radar, cameras, etc.) to determine whether or not the dangerous situations (lane departures, expected collisions, etc.) are present. In addition, as a method of informing a driver of dangerous situations, there is a method of displaying the dangerous situations on a display device (for instance, flickering of a warning lamp) or notifying of the dangerous situations by voice. However, in a system for warning a driver by flickering of the display device, voice notification, or the like, there is often a case in which the voice notification is inaudible due to noise during high speed driving or it is difficult to audiovisually recognize the flickering or voice notification when the driver concentrates on driving while keeping eyes forward or falls asleep at the wheel. In addition, it is also important to grasp a driver's mental and physical condition for safe driving. However, it may be difficult to grasp whether or not serious issues, such as a driver's seizure or abnormal emotion status, labored respiration, neglect of observation, drowsiness, and anxiety, in regard to the driver's mental and physical condition, is generated.

Figure 1:
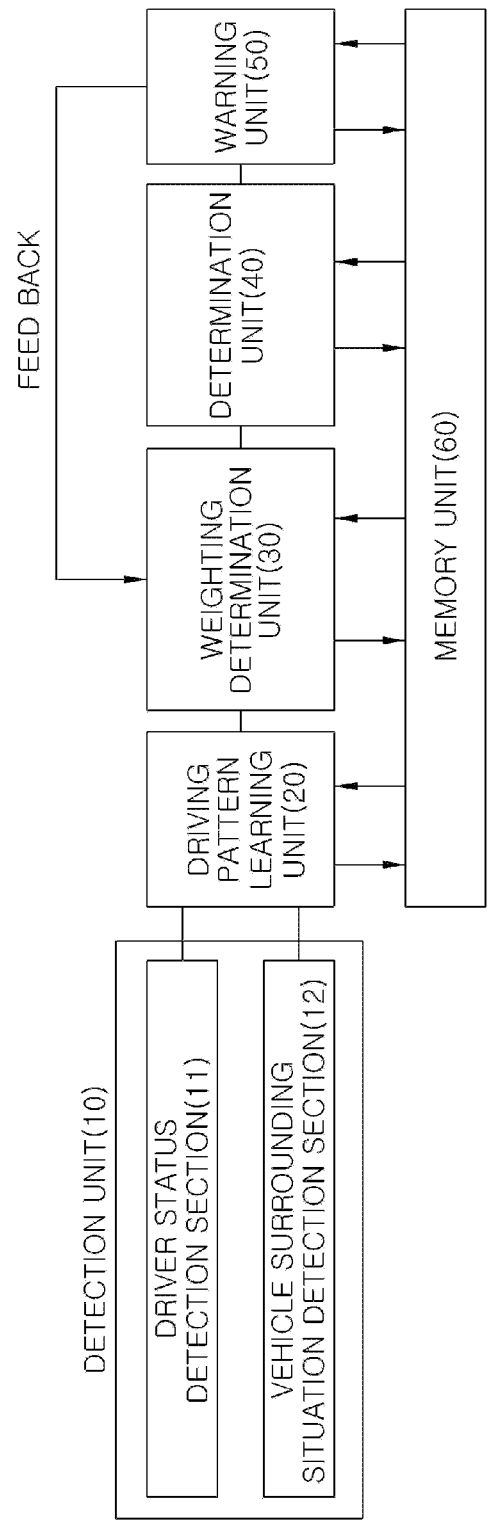
FIG. 1 is a block diagram schematically illustrating a situation detection apparatus according to an embodiment of the present invention.
Figure 2:
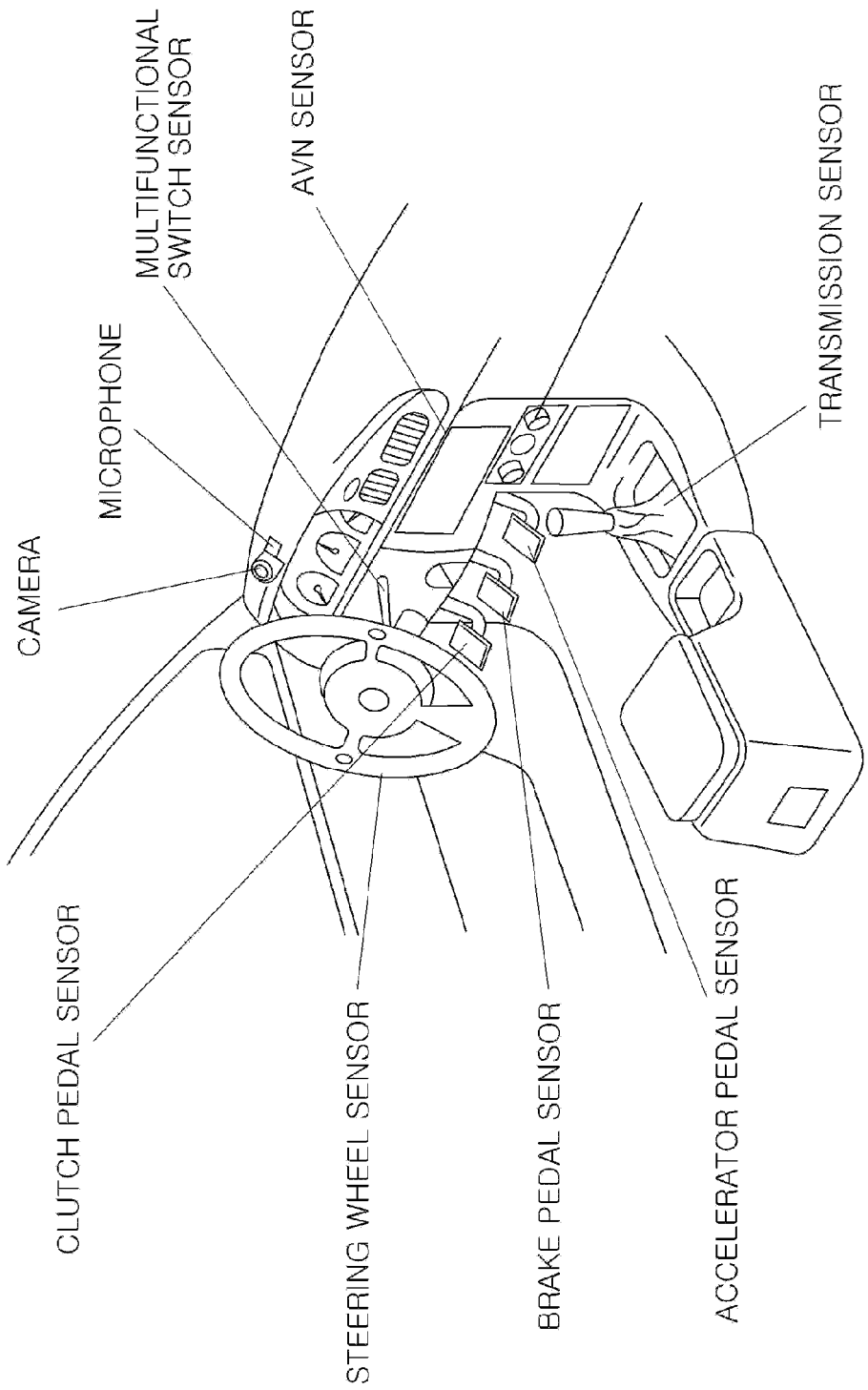
FIG. 2 is an illustrative view of a driver status detection section.
Figure 3:
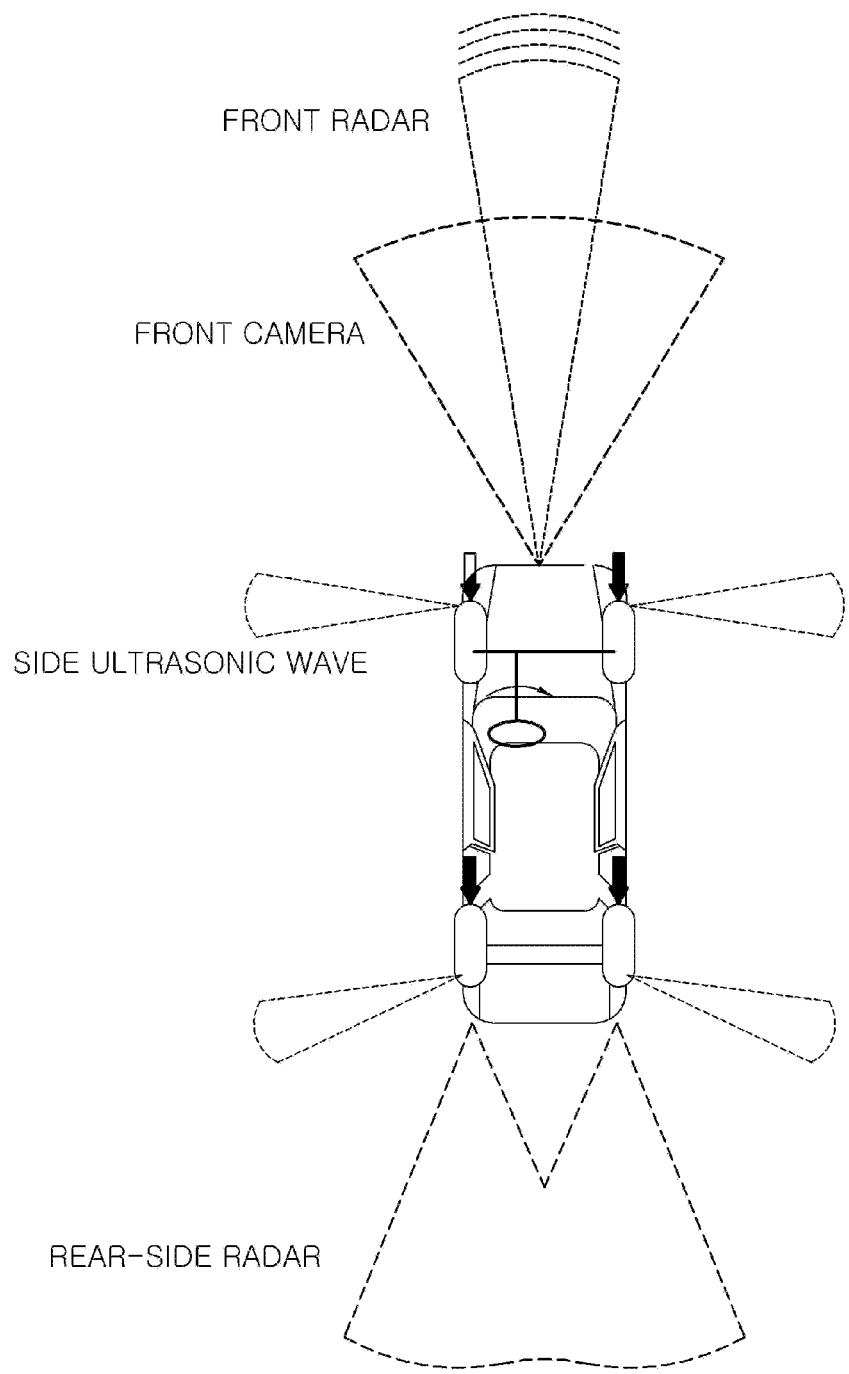
FIG. 3 is an illustrative view of a vehicle surrounding situation detection section.
Figure 4:
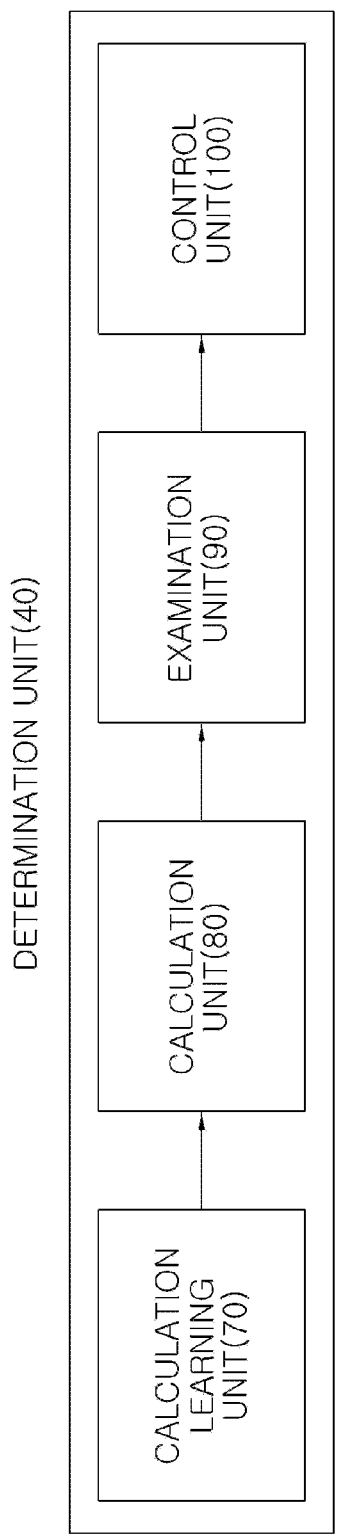
FIG. 4 is a block diagram illustrating a determination unit.
Figure 5:
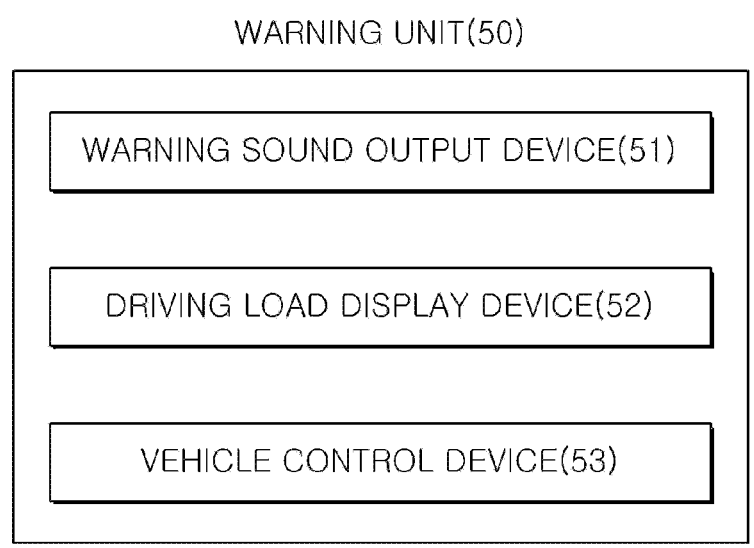
FIG. 5 is a block diagram illustrating a warning unit.

FIG. 1 is a block diagram schematically illustrating a situation detection apparatus according to an embodiment of the present invention. FIG. 2 is an illustrative view of a driver status detection section of FIG. 1. FIG. 3 is an illustrative view of a vehicle surrounding situation detection section of FIG. 1. FIG. 4 is a block diagram illustrating a determination unit of FIG. 1. FIG. 5 is a block diagram illustrating a warning unit of FIG. 1. Referring to FIGS. 1 to 5, the situation detection apparatus according to the embodiment of the present invention includes a detection unit 10, a driving pattern learning unit 20, a weighted value determination unit 30, a determination unit 40, a warning unit 50, and a memory unit 60. The detection unit 10, the driving pattern learning unit 20, the weighted value determination unit 30, the determination unit 40, the warning unit 50, and the memory unit 60 may also be interconnected in a wireless manner using Bluetooth, ZigBee, WiFi, etc. or in a wired manner using RS-232, RS-485, CAN, etc.

A driver status detection section 11 is a component to acquire vehicle driving information, vehicle operation information, and driver status information. The vehicle driving information means, for example, information such as how often a driver steps on an accelerator pedal, how often a driver steps on a brake pedal, how often a driver operates a steering wheel, and how often a driver operates a multifunctional switch. In addition, in a manual transmission vehicle, the driving information may include information such as how often a driver steps on a clutch pedal and how often a driver operates a transmission, besides the above information. The multifunctional switch means a switch of a wiper, a turn signal indicator, a lighting lamp, or the like. Since the multifunctional switch is a factor necessary to vehicle driving, operation information of the multifunctional switch may be included in the vehicle driving information. The vehicle operation information may include, for example, information such as how often a driver operates an AVN (Audio Video Navigation) and how often a driver operates an air conditioning device. The driver status information may include, for example, information such as how long a driver makes conversation (including a telephone conversation), whether or not a driver drowses, whether or not a driver keeps eyes forward, and whether or not abnormality is generated in a driver's electrocardiogram or brainwave. The detection unit 10 is a component to identify a driver and acquire driver status data, vehicle driving information data and vehicle surrounding obstacle data. The detection unit 10 includes a driver status detection section 11 and a vehicle surrounding situation detection section 12.

The driver status detection section 11 may include one or more of an infrared LED imaging device, a steering wheel speed detection sensor, a steering wheel angle detection sensor, a suspension movement detection sensor, a pedal operation detection sensor, a multifunctional switch operation detection sensor, a voice recognition sensor, an AVN operation detection sensor, an air conditioning device operation detection sensor, a gearbox sensor, a console box operation detection sensor, and a glove box operation detection sensor. The driver status detection section 11 also acquires information about driver operation and behavior, which are not directly related to driving, so as to provide reasons for situation determination. The driver status detection section 11 acquires image data of pupils and faces through the infrared LED imaging device. Thus, the current driver is identified. The driver status detection section 11 acquires eyelid detection data to determine whether or not a driver drowses and pupil direction data to determine whether or not a driver keeps eyes forward through the infrared LED imaging device. In addition, the driver status detection section 11 acquires data generated by operations of an accelerator pedal, a brake pedal, a steering wheel, a multifunctional switch, etc. The driver status detection section 11 acquires data about how long a driver makes conversation (including a telephone conversation) by recognizing a voice of the driver. The driver status detection section 11 acquires data about how often a driver operates peripheral devices such as an AVN, an air conditioning device, a gearbox, a console box, and a glove box.

The vehicle surrounding situation detection section 12 is a component to acquire self-vehicle driving information and surrounding vehicle driving information. The self-vehicle driving information means, for example, information such as a self-vehicle speed, a yaw rate, a steering angle, an acceleration, a steering wheel angle change amount, and an angular speed in a self-vehicle. The surrounding vehicle driving information means, for example, information such as a surrounding vehicle speed, a yaw rate, a steering angle, an acceleration, a steering wheel angle change amount, and an angular speed in a surrounding vehicle. To this end, the vehicle surrounding situation detection section 12 may include one or more of a self-vehicle speed sensor, a yaw rate sensor, a steering angle sensor, an acceleration sensor, a steering wheel sensor, front/rear radars, front/rear cameras, side ultrasonic devices, an AVM (Around View Monitoring System) camera, an SCC (Smart Cruise Control), an LKAS (Lane Keeping Assistant System), an SPAS (Smart Parking Assistant System), and an AVM (Around View Monitoring). The vehicle surrounding situation detection section 12 collects the self-vehicle driving information and the surrounding vehicle driving information such as surrounding obstacles and surrounding environments, thereby enhancing reliability when a degree of risk is determined during driver's driving.

The driving pattern learning unit 20 learns a driver's driving pattern (updates data) and stores learned data in the memory unit 60, based on the data acquired by the detection unit 10.

In a case of a new driver, the driving pattern learning unit 20 calls a pre-stored default driving pattern to execute situation detection and newly allocates memory to begin learning. The pre-stored default driving pattern may be an average driving pattern of a plurality of drivers defined by experiment. Thus, it may be possible to induce the new driver to drive the vehicle with safety corresponding to the driving of the new driver, unlike the related art. The driving pattern learning unit 20 learns and stores a driving pattern within a preset learning range. A possibility of unnecessary warning is increased when a driving pattern such as rapid acceleration, rapid brake, or rapid rotation according to unexpected situations during driving is learned under the same condition. Accordingly, in order to remove such noise, a driving pattern, which is a subject to be learned, is restricted to the driving pattern within a preset learning range. The preset range may be determined by experiment according to conditions of test subjects.

The weighted value determination unit 30 determines a weighted value assigned to the information data acquired by the detection unit 10, based on the driving pattern learned by the driving pattern learning unit 20. This is to induce safe driving by providing a situation detection and warning system specified for each driver according to the learned driving pattern. For example, when a driver A frequently operates the accelerator pedal, the brake pedal, the multi-functional switch, or the like, a weighted value of operation information data of such a device is set high, and when a driver B frequently operates the AVN switch, the air conditioning device, or the like, a weighted value of operation information data of such devices is set high. The weighted value may be determined by experiment according to conditions of test subjects. Thus, a weighted value is also determined about the new driver and thus the situation detection of the vehicle may be performed. The determined weighted value is changed as in the following equation, by comparing acquired information data and a calculated integrated risk index with an information data reference value and an integrated risk index reference value, by feedback from the warning unit 50. Thus, it may be possible to induce safe driving by providing the situation detection and warning system specified for each driver according to the driver's driving pattern.

$$\alpha(n+1)=\alpha(n), \text{ if } W<d_W \text{ and } R\geq d_R$$

$$\alpha(n+1)=\alpha(n)+\delta, \text{ if } W\geq d_W$$

$$\alpha(n+1)=\alpha(n)-\delta, \text{ if } W<d_W \text{ and } R<d_R,$$

where R=integrated risk index,
$\alpha$=weighting,
$\alpha(n+1)$=weighted value changed by feedback,
$\alpha(n)$=weighted value before change,
$\alpha W$=acquired information data,
$d_R$=integrated risk index reference value,
$d_W$=information data reference value, and
$\delta=\alpha(n)/R$.

In the above equation, $d_W$ refers to an information data reference value and $d_R$ refers to an integrated risk index reference value. The weighted value determination unit 30 compares current R and W values with respective reference values and changes the weighted value as in FIG. 8 and the above equation. In addition, $\alpha(n+1)$ refers to a weighted value changed by feedback and $\alpha(n)$ refers to a weighted value before change. In addition, $\delta$ refers to a rate occupied by a weighted value before change of each information data in the integrated risk index and the weighted value of each information data may be increased or decreased by a $\delta$ value.

The determination unit 40 is a component which determines a safe driving state of a driver, based on the data to which the weighted value determined by the weighted value determination unit 30 is assigned. The determination unit 40 includes a calculation learning unit 70, a calculation unit 80, an examination unit 90, and a control unit 100.

The calculation learning unit 70 arranges data, to which the weighted value determined by the weighted value determination unit 30 is assigned, in the order of data causing the integrated risk index to exceed a preset reference risk index and selects only a plurality of high data. The situation detection apparatus of the present invention collects a great deal of data from a plurality of sensors inside/outside the vehicle to accurately detect situations. However, when a considerable time is required in processing a great deal of data, it is deviated from the purpose of the present invention for preventing accidents and inducing safe driving. Accordingly, there is a need to select some data from a great deal of data and perform rapid calculation during driving required for instantaneous determination. Thus, learning for rapid calculation and data selection are performed in the calculation learning unit 70. A selection function of the calculation learning unit 70 is initially inactivated and the calculation learning unit 70 stores results arising from the control unit 100. Subsequently, when data equal to or more than a certain number of times are stored, the calculation learning unit 70 arranges the data in the order of data mainly causing the integrated risk index calculated by the calculation unit 80 to exceed a preset reference risk index and selects only a plurality of high data. Here, the selected data is used for calculation and the remaining data is ignored such that calculation speed is increased.

For example, when risk warnings equal to or more than 5000 times are generated and risk index data equal to or more than 5000 times are stored, data causing the calculated integrated risk index to exceed a preset reference risk index is selected. That is, the highest three data may be selected from data to which the weighted value is reflected by analysis of causes such as the number of times of operation of the brake pedal, a steering wheel angle change amount, a forward observation neglect of a driver, and a trajectory of a surrounding vehicle.

Subsequently, calculation speed may be increased in such a manner that only the selected data is reflected to calculate the integrated risk index and the remaining data is not reflected to calculate the integrated risk index. The data selected by the calculation learning unit 70 is transferred to the calculation unit 80.

The calculation unit 80 calculates some data selected by the calculation learning unit 70 among data, to which the weighted value determined by the weighted value determination unit 30 is assigned, according to a preset calculation equation and calculates an integrated risk index. For example, a driver's integrated risk index may be calculated by adding up respective risk indexes which multiply data selected by the calculation learning unit 70 by a weighted value for each data assigned by the weighted value determination unit, as in the following equation.

$$R = \alpha_A \times W_A + \alpha_B \times W_B + \alpha_C \times W_C,$$

where R=integrated risk index,
α=weighted value for each selected information data,
W=selected information data.

The examination unit 90 determines whether a result calculated by the calculation unit 80 is valid. When the calculation learning unit 70 selects some data for rapid calculation and calculation is performed based on the same, there is a possibility of error occurring in the calculated result. Since the object of the present invention is to induce safe driving, an examination process for error removal is required for driver's safe driving. The examination unit 90 compares a risk index calculated by a pre-stored driving pattern of a current driver (hereinafter, referred to as "examination risk index") with an integrated risk index calculated by a driving pattern learning a current driving pattern of the current driver and determines that a calculated risk index value is valid when a difference between the examination risk index and the calculated integrated risk index is within a preset error range. In addition, the integrated risk index is transferred to the control unit 100. The preset error range may be an experimental value according to conditions of test subjects. In addition, the examination risk index may be previously calculated before current driving of the driver and stored in the memory unit 60.

The control unit 100 compares the integrated risk index transferred from the examination unit 90 with a preset reference risk index and serves to activate the warning unit 50 according to the compared result.

The warning unit 50 is a component which warns a driver that the driving state of the driver is not in a safe driving state to induce the safe driving by the determination unit 40, and includes a warning sound output device 51, a driving load display device 52, and a vehicle control device 53. When the driving state of the driver is determined to be not in the safe driving state by the determination unit 40, the warning sound output device 51 may generate a warning sound to the driver or play an announcement for notifying that the driver is not in the safe driving state. The warning sound output device 51 may also utilize a speaker installed to the vehicle. The driving load display device 52 may also display a driving load through an instrument panel, an AVN, or an HUD (Head Up Display) in the vehicle. The vehicle control device 53 is a device to safely stop the vehicle when the driver is determined to be not in the safe driving state, and may be a device for controlling a steering wheel, a transmission, and a brake which are installed to the vehicle. The memory unit 60 may store and call information such as driver information, driver's driving pattern information, a preset weighting, a preset error range, a pre-stored examination risk index, and a preset reference risk index. The memory unit 60 may be a non-volatile memory as a storage means for storing data. For example, the driver information of a driver A, a driver B, a driver C, . . . , etc. is stored in the memory unit 60 and the driving pattern information corresponding to each driver is stored in the form of "driver A—driving pattern A", "driver B—driving pattern B", "driver C—driving pattern C", . . . , etc. in the memory unit 60. In this case, the data acquired by the detection unit 10, such as the number of times of operation of the accelerator pedal for unit time and the number of times of operation of the brake pedal for unit time, are included in each driving pattern.

Figure 6:
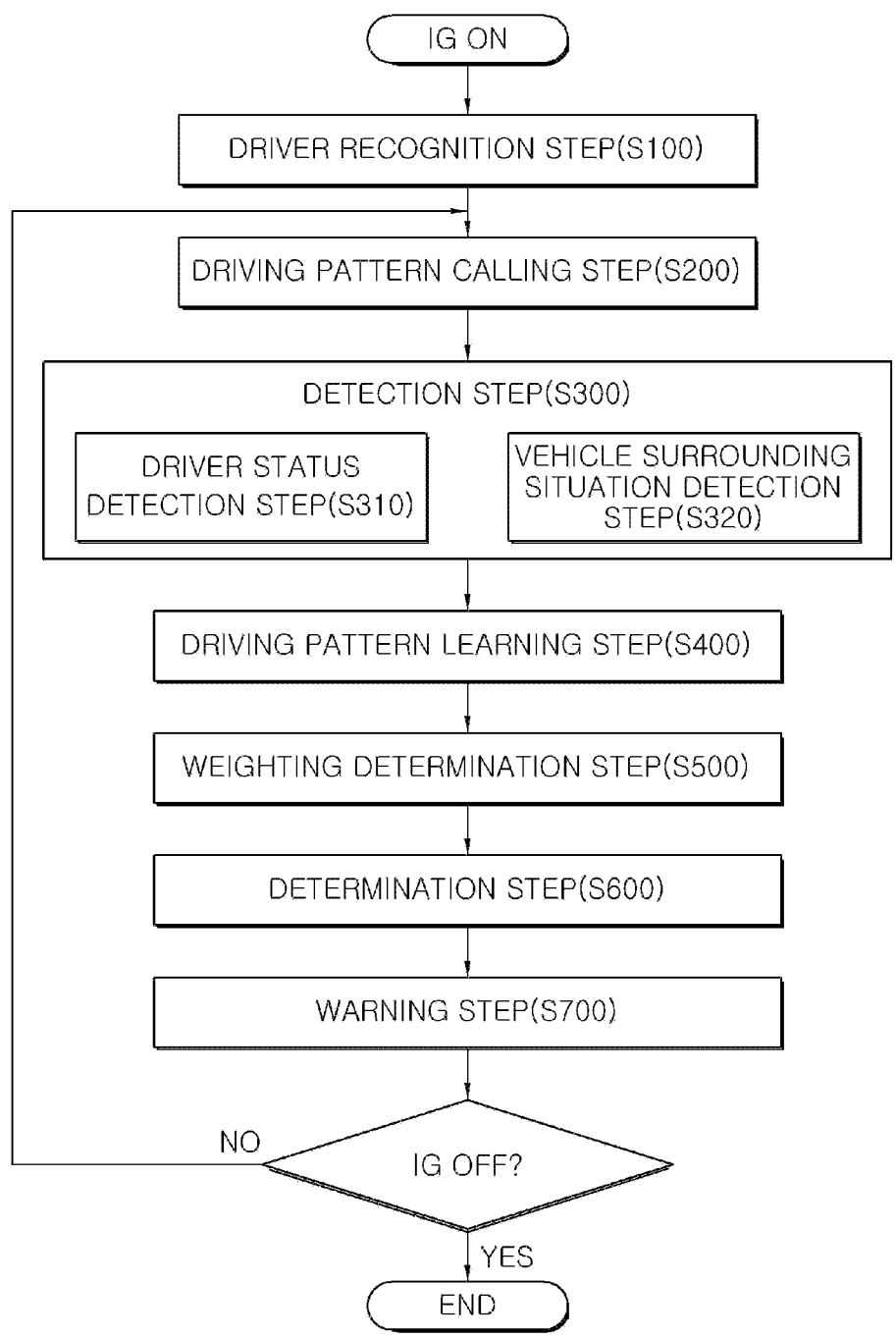
FIG. 6 is a flowchart schematically illustrating a situation detection method according to another embodiment of the present invention.
Figure 7:
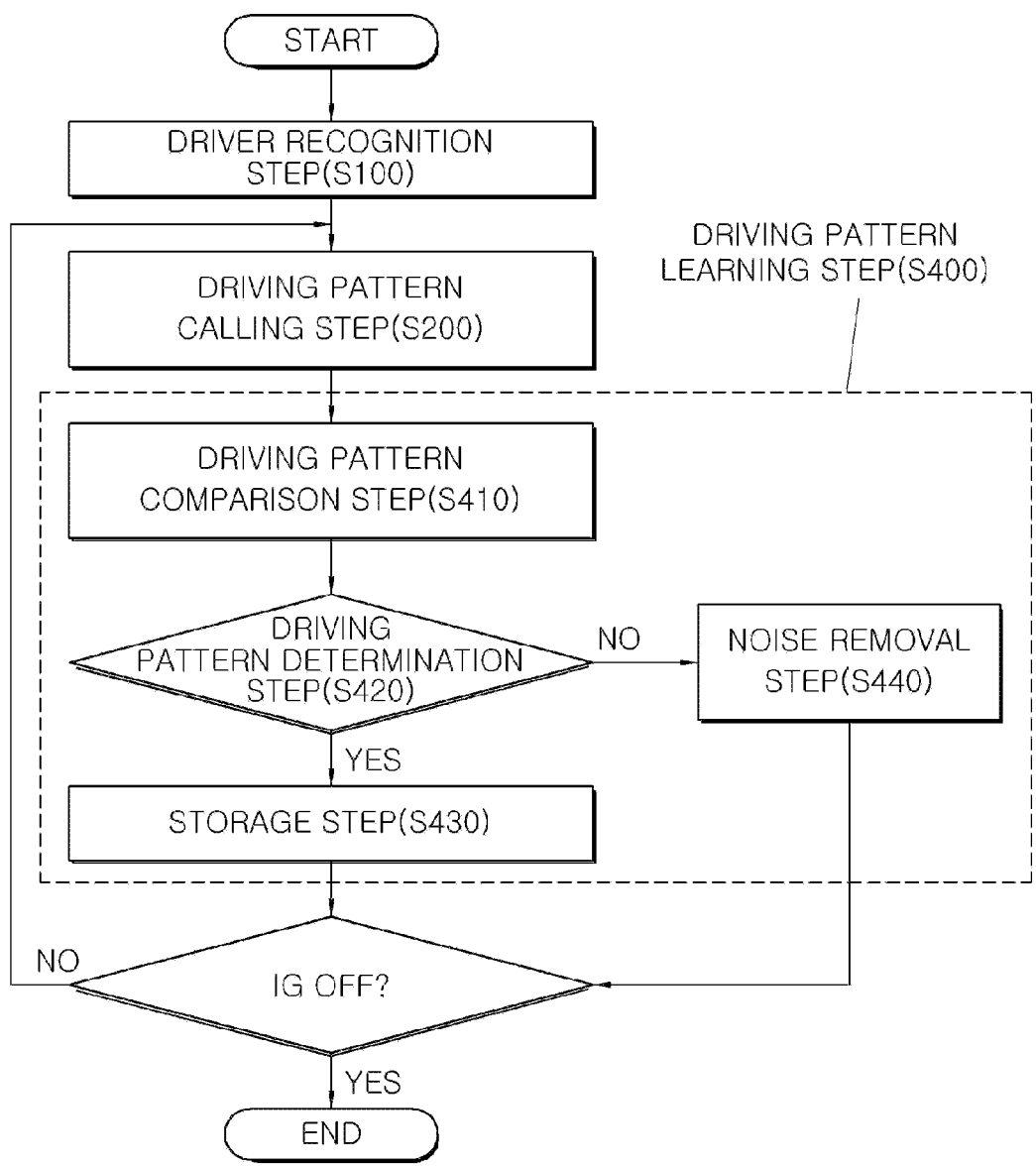
FIG. 7 is a flowchart illustrating a driving pattern learning step.
Figure 8:
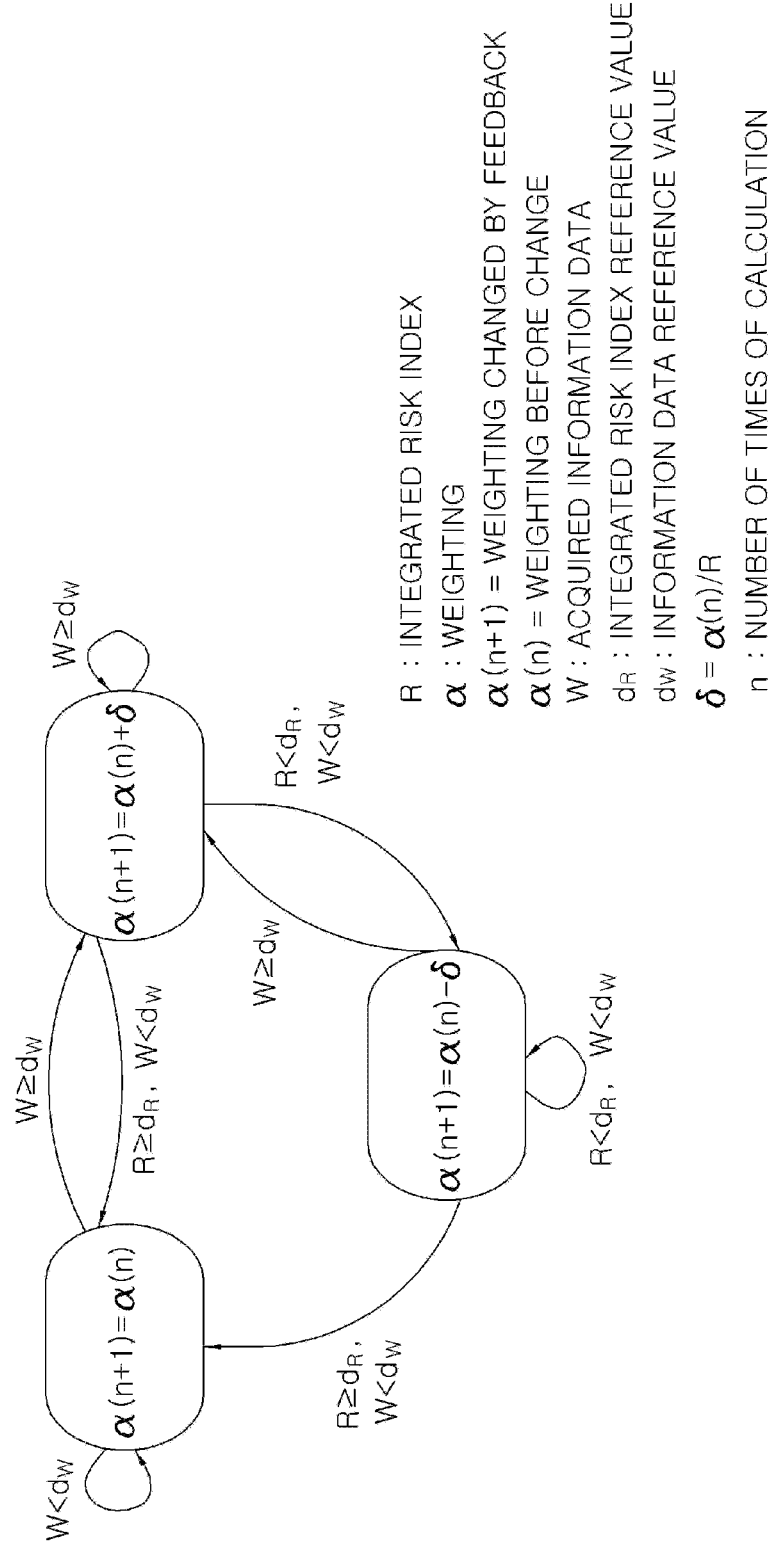
FIG. 8 is a view illustrating a state in a weighted value determination step.
Figure 9:
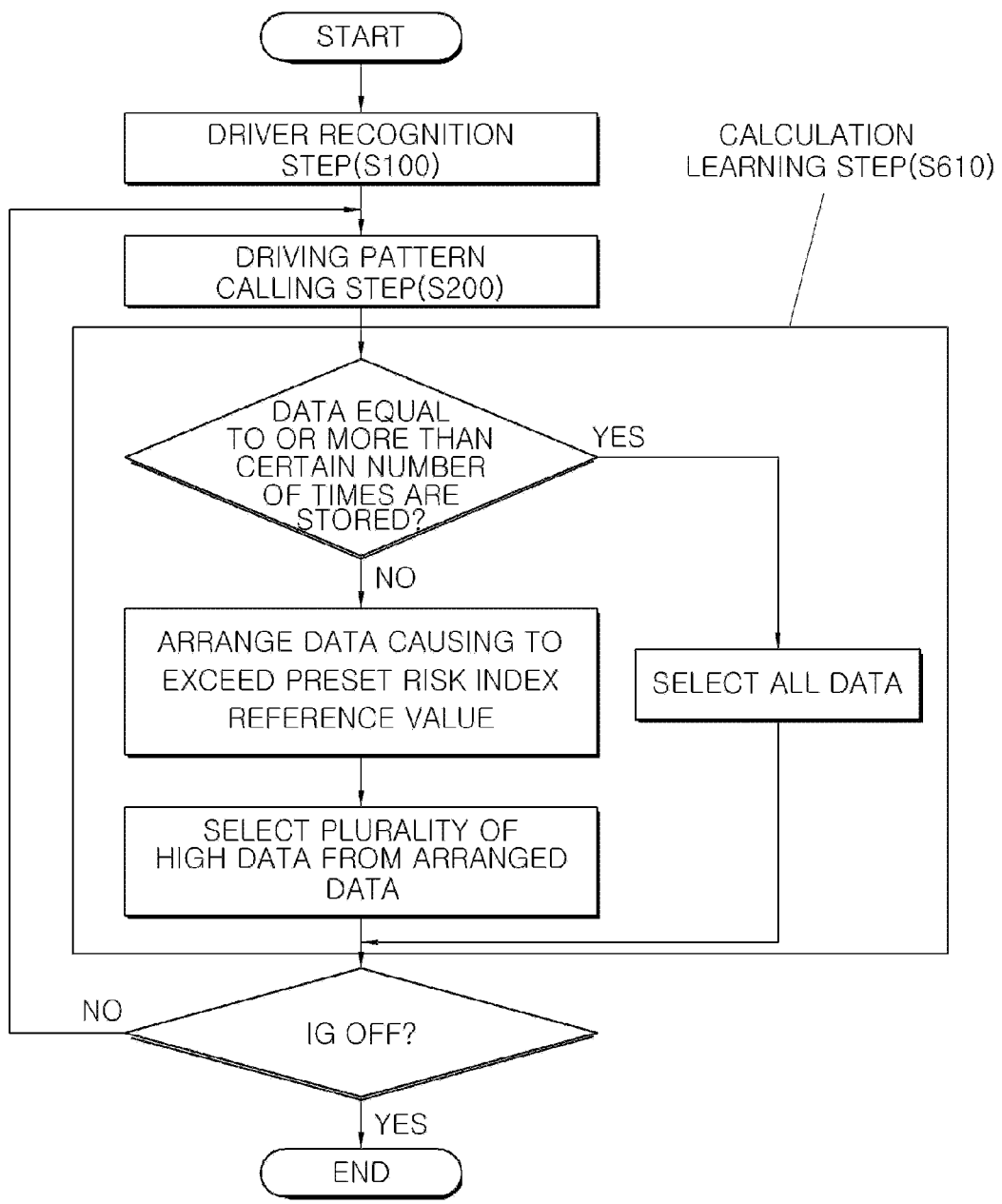
FIG. 9 is a flowchart illustrating a calculation learning step.
Figure 10:
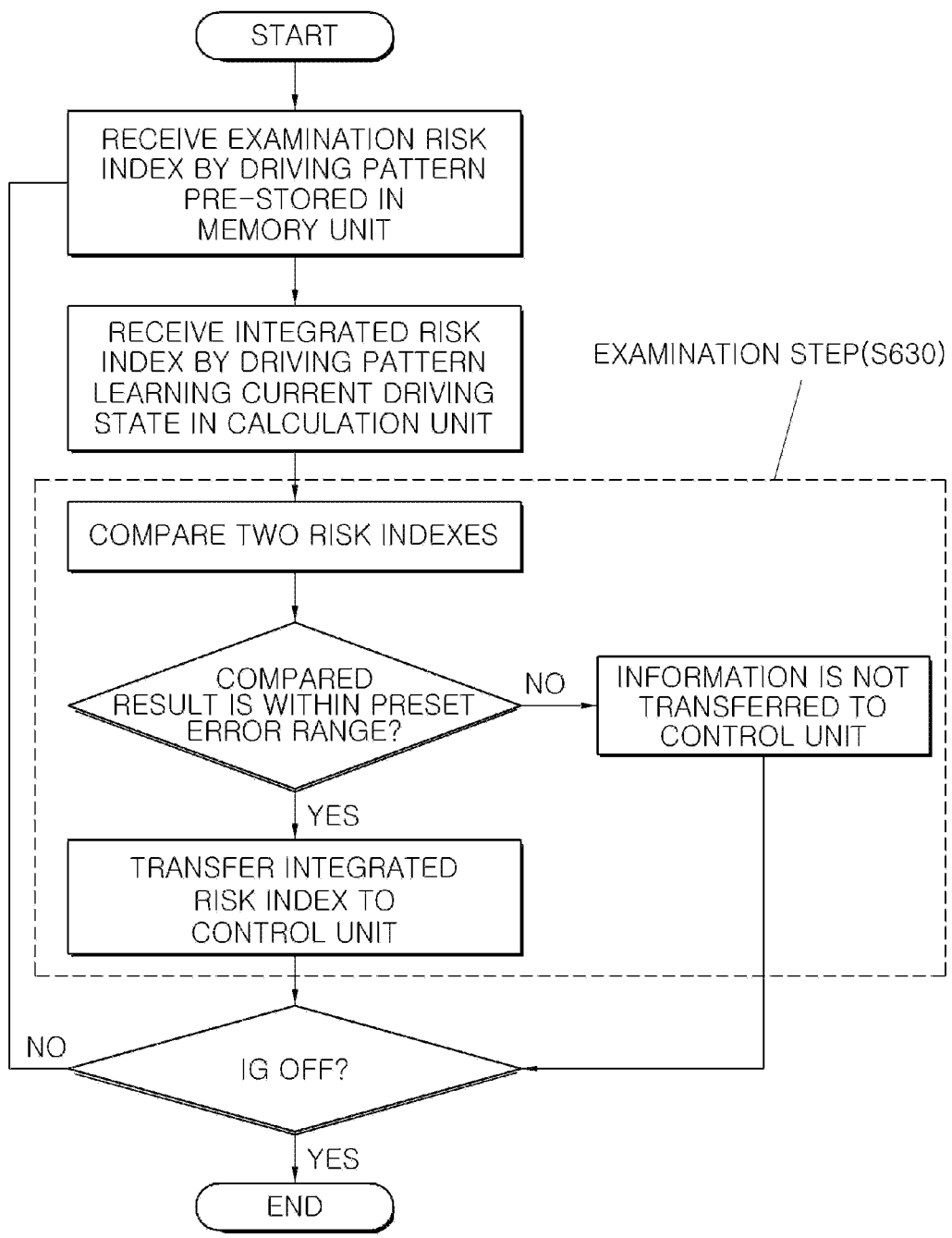
FIG. 10 is a flowchart illustrating an examination step.
Figure 11:
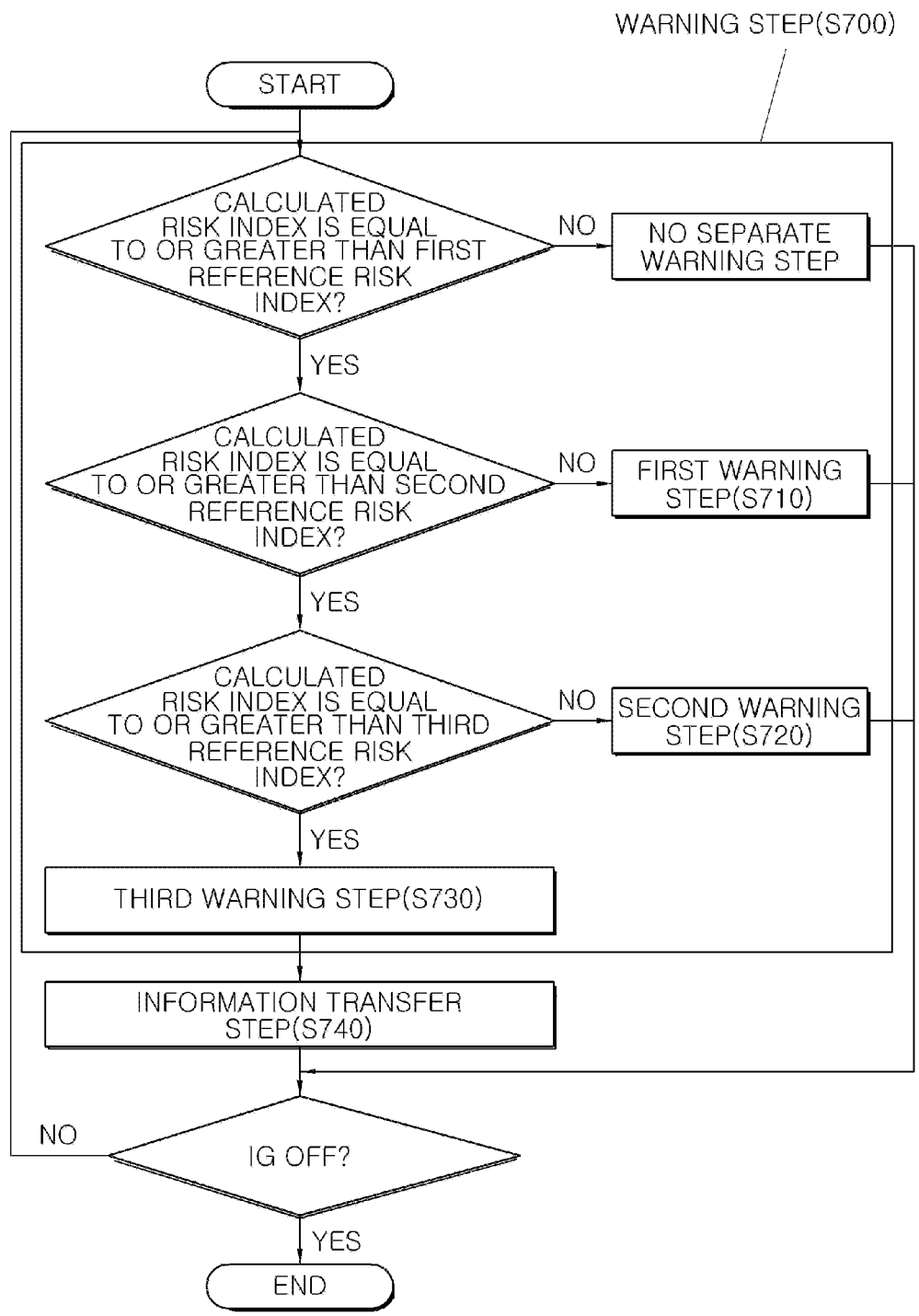
FIG. 11 is a flowchart illustrating a warning step.
Figure 12A:
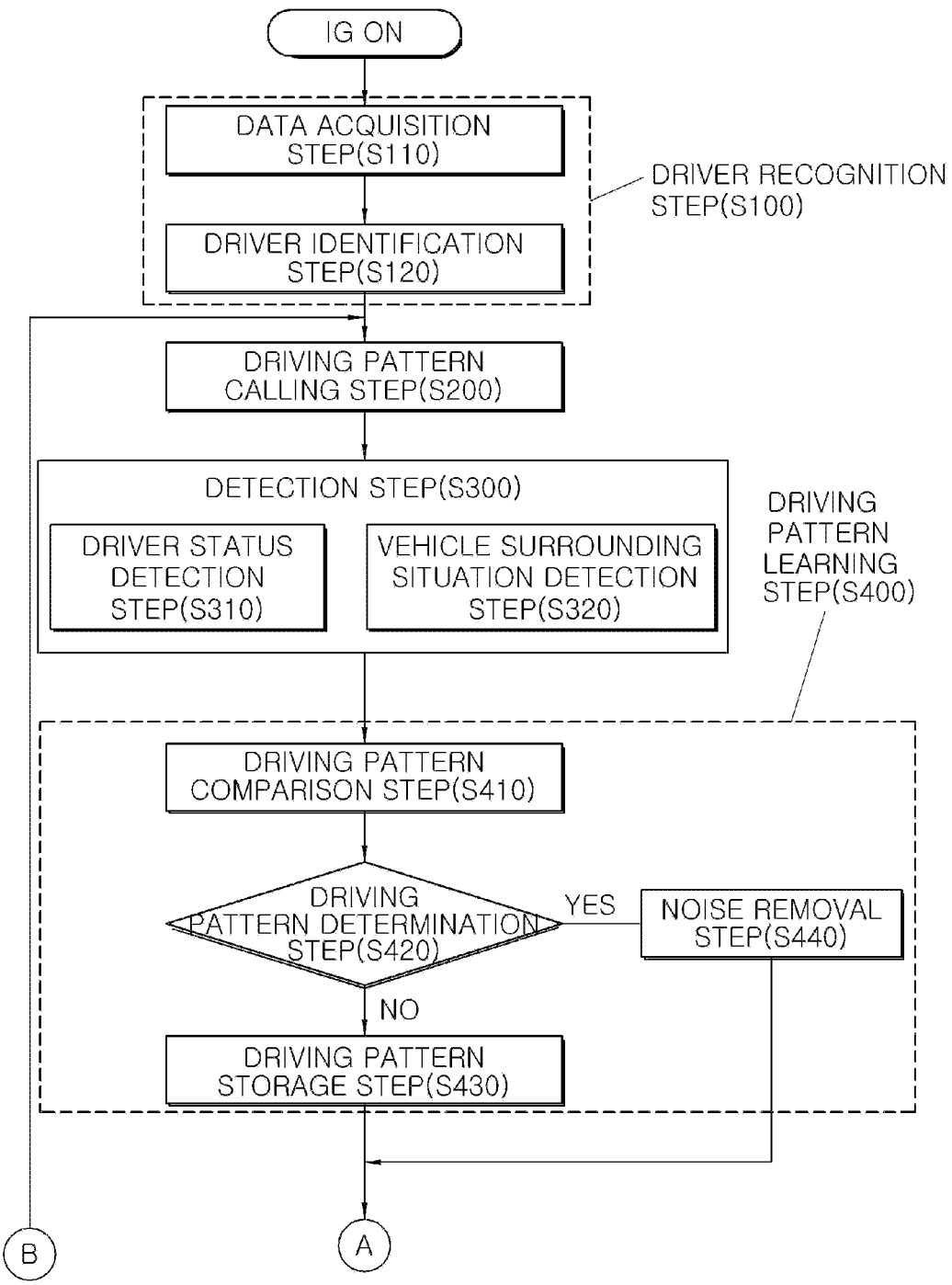
FIGS. 12A, 12B, and 12C are detailed flowcharts illustrating the situation detection method.
Figure 12B:
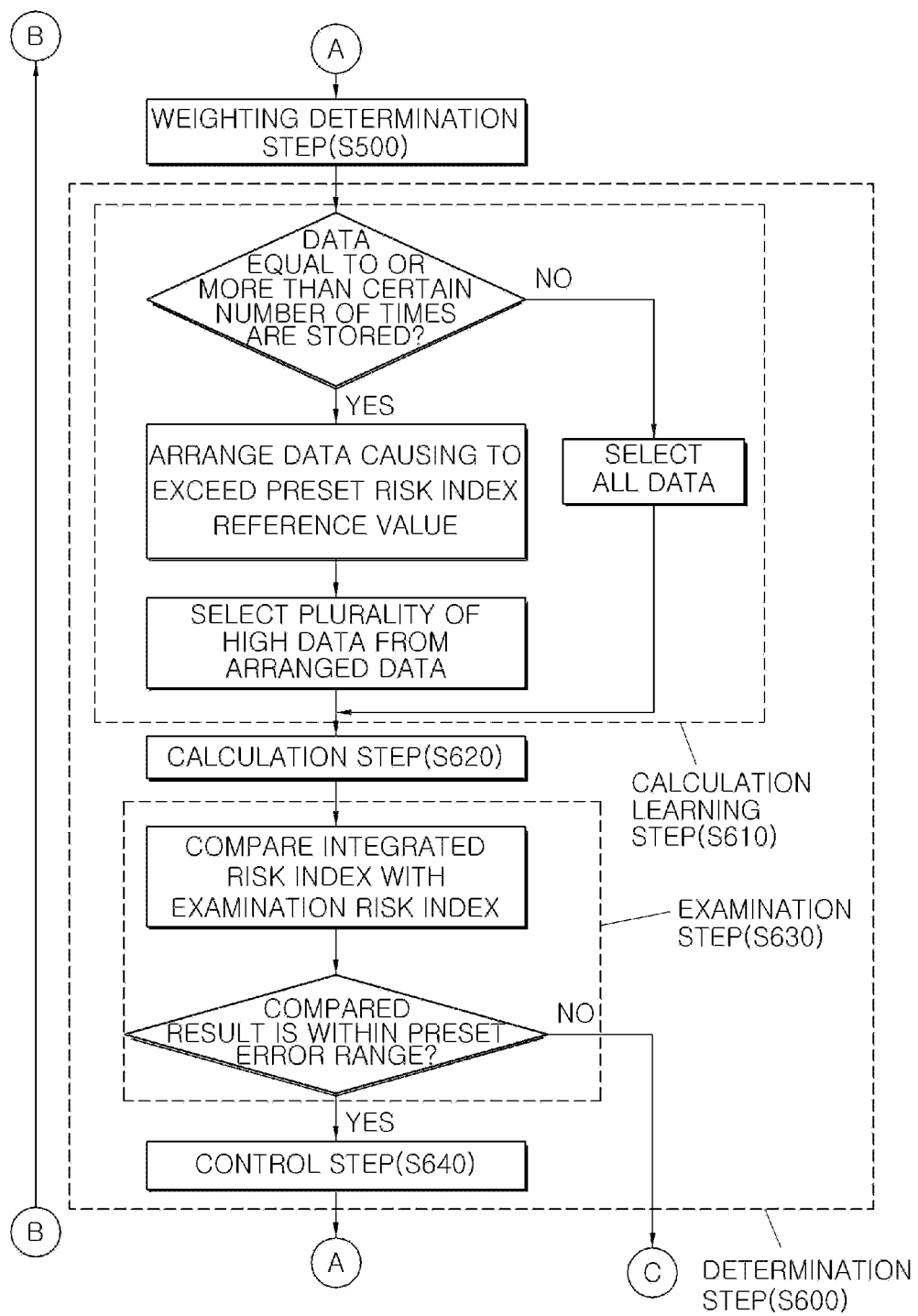
Figure 12C:
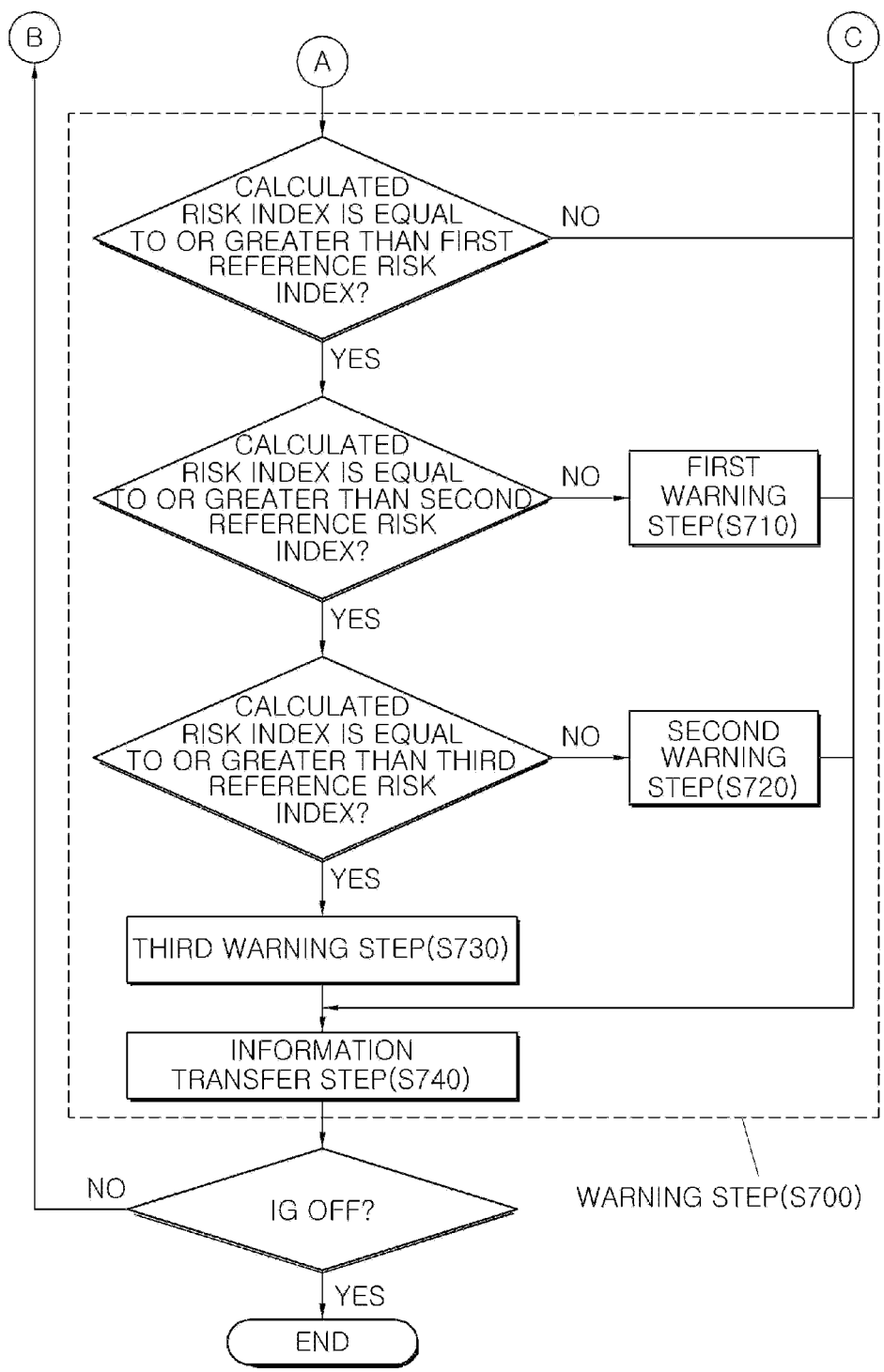

FIG. 6 is a flowchart schematically illustrating a situation detection method according to another embodiment of the present invention. FIG. 7 is a flowchart illustrating a driving pattern learning step. FIG. 8 is a view illustrating a state in a weighted value determination step. FIG. 9 is a flowchart illustrating a calculation learning step. FIG. 10 is a flowchart illustrating an examination step. FIG. 11 is a flowchart illustrating a warning step. FIGS. 12A, 12B, and 12C are detailed flowcharts illustrating the situation detection method. Referring to FIGS. 6 to 12C, the situation detection method according to another embodiment of the present invention includes a driver recognition step S100, a driving pattern calling step S200, a detection step S300, a driving pattern learning step S400, a weighted value determination step S500, a determination step S600, and a warning step S700.

The driver recognition step S100 is a step of calling pre-stored driver information to compare whether the driver information coincides with a current driver, and includes a driver data acquisition step S110 and a driver identification step S120. The driver data acquisition step S110 is a step of acquiring image data of pupils or faces through an imaging device and the driver identification step S120 is a step of comparing the image data of pupils or faces acquired by the driver data acquisition step S110 with the driver information pre-stored in a memory unit 60 to identify a driver.

The driving pattern calling step S200 is a step of calling a pre-stored driving pattern of the driver identified by the driver identification step S120 from the memory unit 60. If the driver coinciding with the pre-stored driver information is not present because of a new driver, a pre-stored default driving pattern is called. The pre-stored default driving pattern may be an average driving pattern of a plurality of drivers defined by experiment. Thus, it may be possible to induce the new driver to drive a vehicle with safety corresponding to the driving of the new driver even in a case of the new driver, unlike the related art.

The detection step S300 is a step of collecting driver status information and vehicle driving information or vehicle surrounding obstacle information, and includes a driver status detection step S310 and a vehicle surrounding situation detection step S320.

The driver status detection step S310 is a step of collecting driver status information and acquires vehicle driving information, vehicle operation information, and driver status information. The vehicle driving information means, for example, information such as how often a driver steps on an accelerator pedal, how often a driver steps on a brake pedal, how often a driver operates a steering wheel, and how often a driver operates a multifunctional switch. In addition, in a manual transmission vehicle, the driving information may include information such as how often a driver steps on a clutch pedal and how often a driver operates a transmission, besides the above information. The multifunctional switch means a switch of a wiper, a turn signal indicator, a lighting lamp, or the like. Since the multifunctional switch is a factor necessary to vehicle driving, operation information of the multifunctional switch may be included in the vehicle driving information.

The vehicle operation information may include, for example, information such as how often a driver operates an AVN (Audio Video Navigation), how often a driver operates an air conditioning device, and how often a driver operates peripheral devices such as a gearbox, a console box, and a glove box. The driver status information may include, for example, information such as how long a driver makes conversation (including a telephone conversation), whether or not a driver drowses, whether or not a driver keeps eyes forward, and whether or not abnormality is generated in a driver's electrocardiogram or brainwave.

To this end, the driver status detection step S310 may detect one or more of a driver eyelid, a driver pupils, a steering wheel speed, a steering wheel angle, a suspension movement, whether or not an accelerator pedal is operated, whether or not a brake pedal is operated, whether or not a multifunctional switch is operated, whether or not a driver makes conversation, whether or not an AVN is operated, whether or not an air conditioning device is operated, whether or not a gearbox is operated, whether or not a console box is operated, and whether or not a glove box is operated.

The vehicle surrounding situation detection step S320 acquires self-vehicle driving information, surrounding vehicle driving information, vehicle surrounding obstacle information, etc. The self-vehicle driving information means, for example, information such as a self-vehicle speed, a yaw rate, a steering angle, an acceleration, a steering wheel angle change amount, and an angular speed in a self-vehicle. The surrounding vehicle driving information means, for example, information such as a surrounding vehicle speed, a yaw rate, a steering angle, an acceleration, a steering wheel angle change amount, and an angular speed in a surrounding vehicle. The vehicle surrounding obstacle information means, for example, information such as a traffic situation of a forward road, a road shape, and a road surface state. The vehicle surrounding situation detection step S320 detects a vehicle surrounding situation using one or more of an SCC (Smart Cruise Control), an LKAS (Lane Keeping Assistant System), an SPAS (Smart Parking Assistant System), an AVM (Around View Monitoring), a camera, and a radar. The vehicle surrounding situation detection step S320 collects the self-vehicle driving information and the surrounding vehicle driving information such as surrounding obstacles and surrounding environments, thereby enhancing reliability when a degree of risk is determined during a driver's driving.

The driving pattern learning step S400 is a step of learning a pre-stored driving pattern of the driver called by the driving pattern calling step S200 and a driving pattern by the data acquired from the detection step S300 to store the learned driving pattern in the memory unit 60, and includes a driving pattern comparison step S410, a driving pattern determination step S420, a driving pattern storage step S430, and a noise removal step S440. In a case of the new driver, the driving pattern learning step S400 calls a pre-stored default driving pattern to execute situation detection and newly allocates memory to begin learning. The pre-stored default driving pattern may be an average driving pattern of a plurality of drivers defined by experiment. Thus, it may be possible to induce the new driver to drive the vehicle with safety corresponding to the driving of the new driver, unlike the related art. In addition, a specific driving pattern for each driver may be grasped by performing of the driving pattern learning step S400 and thus a situation detection method specified for each driver may be provided to induce safe driving.

The driving pattern comparison step S410 is a step of comparing a pre-stored driving pattern of the driver called by the driving pattern calling step S200 and a current driving pattern by the data acquired from the detection step S300. The driving pattern determination step S420 is a step of determining whether a difference of both in the driving pattern comparison step S410 is within a preset noise range. The driving pattern storage step S430 is a step of learning a current driving pattern when the difference of both is equal to or less than the preset noise range in the driving pattern determination step S420 to store the learned driving pattern in the memory unit 60. The noise removal step S440 is a step of excluding a current driving pattern from a subject to be learned when the difference of both exceeds the preset noise range in the driving pattern determination step S420. The preset noise range may be an experimental value according to conditions of test subjects.

The driving pattern learning step S400 learns and stores a driving pattern within a preset noise range. A possibility of unnecessary warning is increased when a driving pattern such as rapid acceleration, rapid brake, or rapid rotation according to unexpected situations during driving is learned under the same condition. Accordingly, the driving pattern learning step S400 is to remove such noise. The preset noise range may be determined by experiment according to conditions of test subjects.

The weighted value determination step S500 is a step of determining a weighted value assigned to each data acquired from the detection step S300, based on the driving pattern learned in the driving pattern learning step S400. This is to induce safe driving by providing a situation detection and warning system specified for each driver according to the learned driving pattern. For example, when a driver A frequently operates the accelerator pedal, the brake pedal, the multifunctional switch, or the like, a weighted value of operation information data of such a device is set high, and when a driver B frequently operates the AVN switch, the air conditioning device, or the like, a weighted value of operation information data of such devices is set high.

The weighted value may be determined by experiment according to conditions of test subjects. Thus, a weighted value is also determined about the new driver and thus the situation detection of the vehicle may be performed. The determined weighted value is changed as in the following equation by feedback from an information transfer step S740 of the warning step S700. Thus, it may be possible to induce safe driving by providing the situation detection and warning system specified for each driver according to the driver's driving pattern.

$\alpha(n+1)=\alpha(n)$, if $W<d_W$ and $R \geq d_R$ $\alpha(n+1)=\alpha(n)+\delta$, if $W \geq d_W$ $\alpha(n+1)=\alpha(n)-\delta$, if $W<d_W$ and $R<d_R$, where R=integrated risk index,
α=weighting,
α(n+1)=weighted value changed by feedback, α(n)=weighted value before change,
W=acquired information data,
$d_R$=integrated risk index reference value,
$d_W$=information data reference value, and
δ=α(n)/R.

In the above equation, $d_W$ refers to an information data reference value and $d_R$ refers to an integrated risk index reference value. The weighted value determination step S500 compares current R and W values with respective reference values and changes the weighted value as in FIG. 8 and the above equation. In addition, α(n+1) refers to a weighted value changed by feedback and α(n) refers to a weighted value before change. In addition, δ refers to a rate occupied by a weighted value before change of each information data in the integrated risk index and the weighted value of each information data may be increased or decreased by a δ value.

The determination step S600 is a step of determining a safe driving state of a driver, based on the data to which the weighted value determined in the weighted value determination step S500 is assigned. The determination step S600 includes a calculation learning step S610, a calculation step S620, an examination step S630, and a control step S640.

The calculation learning step S610 is a step of arranging data, to which the weighted value determined in the weighted value determination step S500 is assigned, in the order of data mainly causing the integrated risk index to exceed a preset reference risk index and of selecting only a plurality of high data. The situation detection method of the present invention collects a great deal of data from a plurality of sensors inside/outside the vehicle to accurately detect situations. However, when a considerable time is required in processing a great deal of data, it is deviated from the purpose of the present invention for preventing accidents and inducing safe driving. Accordingly, there is a need to select some data from a great deal of data and perform rapid calculation during driving required for instantaneous determination. Thus, learning for rapid calculation and data selection are performed in the calculation learning step S610. A selection function in the calculation learning step S610 is initially inactivated and the calculation learning step S610 stores results arising from the control step S640. Subsequently, when data equal to or more than a certain number of times are stored, the calculation learning step S610 arranges the data in the order of data mainly causing the integrated risk index calculated in the calculation step S620 to exceed a preset reference risk index and selects only a plurality of high data. Here, the selected data is used for calculation and the remaining data is ignored such that calculation speed is increased. For example, when risk warnings equal to or more than 5000 times are generated and risk index data equal to or more than 5000 times are stored, data causing the calculated integrated risk index to exceed a preset reference risk index is selected. That is, the highest three data may be selected from data to which the weighted value is reflected by analysis of causes such as the number of times of operation of the brake pedal, a steering wheel angle change amount, a forward observation neglect of a driver, and a trajectory of a surrounding vehicle. Subsequently, calculation speed may be increased in such a manner that only the selected data is reflected to calculate the integrated risk index and the remaining data is not reflected to calculate the integrated risk index. The data selected in the calculation learning step S610 is transferred to the calculation step S620.

The calculation step S620 is a step of calculating a driver's integrated risk index by adding up respective risk indexes which multiply data selected in the calculation learning step S610 among data, to which the weighted value determined in the weighted value determination step S500 is assign, by a weighted value for each data assigned in the weighted value determination step S500. For example, the risk index may be calculated as in the following equation.

$$R = \alpha_A \times W_A + \alpha_B \times W_B + \alpha_C \times W_C,$$

where R=integrated risk index,
α=weighted value for each selected information data,
W=selected information data.

The examination step S630 is a step of comparing the integrated risk index calculated by the calculation step S620 with a risk index calculated based on a pre-stored driving pattern (hereinafter, referred to as "examination risk index") to determine whether the compared result is within a preset error range. That is, the examination step S630 is a step of determining whether a result calculated by the calculation step S620 is valid. When the calculation learning step S610 selects some data for rapid calculation and calculation is performed based on the same, there is a possibility of error occurring in the calculated result. Since the object of the present invention is to induce safe driving, an examination process for error removal is required for a driver's safe driving. Accordingly, the examination step S630 compares a risk index calculated by a pre-stored driving pattern of a current driver (hereinafter, referred to as "examination risk index") with an integrated risk index calculated by a driving pattern learning a current driving pattern of the current driver and determines that a calculated risk index value is valid when a difference between the examination risk index and the calculated integrated risk index is within a preset error range. In addition, the calculated integrated risk index is transferred to the control step S640. The preset error range may be determined by experiment according to conditions of test subjects. The examination risk index may be previously calculated before current driving of the driver and stored in the memory unit 60. On the other hand, since the calculated integrated risk index is invalid when the difference between the examination risk index and the calculated integrated risk index exceeds the preset error range, the result is ignored.

The control step S640 is a step of comparing, when the difference between the examination risk index and the calculated integrated risk index is determined to be within the preset error range in the examination step S630, the calculated integrated risk index with a preset reference risk index to determine the compared result. That is, the control step S640 is a step of comparing the integrated risk index transferred from the examination step S630 with a preset reference risk index and activating the warning step S700 according to the compared result.

The preset reference risk index may include a first reference risk index, a second reference risk index, and a third reference risk index. Each reference risk index may be determined by experiment according to conditions of test subjects.

When the calculated integrated risk index is equal to or greater than a preset first reference risk index and is less than a preset second reference risk index, the control step S640 transfers a signal allowing a first warning step S710 to be performed. In addition, when the calculated integrated risk index is equal to or greater than a preset second reference risk index and is less than a preset third reference risk index, the control step S640 transfers a signal allowing a second warning step S720 to be performed. In addition, when the calculated integrated risk index is equal to or greater than a preset third reference risk index, the control step S640 transfers a signal allowing a third warning step S730 to be performed.

The warning step S700 is a step of warning a driver when the driver is determined to be not in a safe driving state in the determination step S600, and includes a first warning step S710, a second warning step S720, a third warning step S730, and an information transfer step S740. The warning step S700 serves to induce safe driving by performing respective warning steps of different warning levels depending on the signals transferred from the control step S640 to inform of a warning corresponding to the driver status.

The first warning step S710 is performed when the integrated risk index calculated in the control step S640 is equal to or greater than a preset first reference risk index and is less than a preset second reference risk index, and includes one or more of a warning sound generation step through a speaker S711, a warning display step through an AVN or a HUD S712, and a vibration notification step through vibration of a steering wheel or a seat S713.

The second warning step S720 is a step of holding functions of the AVN when the integrated risk index calculated in the control step S640 is equal to or greater than a preset second reference risk index and is less than a preset third reference risk index.

The third warning step S730 is a step of forcibly stopping a vehicle when the integrated risk index calculated in the control step S640 is equal to or greater than a preset third reference risk index. In this case, the vehicle may be forcibly and safely stopped using an ADAS (Advanced Driver Assistance System) module. The ADAS module may include one or more of an LKAS, an SPAS, and an SCC.

The warning step S700 includes the information transfer step S740 of transferring information to the weighted value determining step S500 for change of the weighted value through feedback. Thus, it may be possible to induce safe driving by providing the situation detection and warning system specified for each driver according to the driver's driving pattern.

As is apparent from the above description, an on-vehicle situation detection apparatus and method according to the embodiments of the present invention may grasp a driver's mental and physical condition relevant to vehicle driving or operations by a driver to determine whether or not the driver drives a vehicle with safety and induce the driver to drive the vehicle with safety in various ways, such as warning signs, generation of warning sound, vibration notification, and forced control of the vehicle, when the driver is determined to be not in a safe driving state so as to protect the driver. Particularly, since the on-vehicle situation detection apparatus and method may grasp serious issues, such as a driver's seizure or abnormal emotion, labored respiration, neglect of observation, and poor driving, in regard to the driver's mental and physical condition, which are difficult to be determined in the related art, so as to protect the driver, it may be very useful. In addition, it may be possible to select some data obstructing the safe driving from a great deal of data and rapidly monitor situations by learning of driving patterns. Furthermore, it may be possible to induce the driver to drive the vehicle with safety by examining a determination result for error removal.

While the present invention has been described with respect to the specific embodiments, it will be apparent to those skilled in the art that various changes and modifications may be made without departing from the spirit and scope of the invention as defined in the following claims.

What is claimed is:
1. An on-vehicle situation detection method comprising:
performing driver recognition of calling pre-stored driver information to compare whether the driver information coincides with a current driver of a vehicle;
performing driving pattern calling of calling a pre-stored driving pattern of the driver identified by the performing driver recognition from a memory unit;
performing detection using at least one sensor, of collecting driver status information and vehicle driving information or vehicle surrounding obstacle information;
performing driving pattern learning of learning the pre-stored driving pattern called by the performing driving pattern calling and a driving pattern derived from the performing detection;
performing weight value determination of determining a weight value for data acquired from the performing detection, based on the driving pattern learned in the performing driving pattern learning;
performing determination of determining a safe driving state of the driver, based on the data to which the weight value determined in the performing weight value determination is assigned; and
performing warning of warning the driver when the driver is determined to be not in the safe driving state in the performing determination,
wherein the performing weight value determination assigns a weight value determined according to impact on a driver's integrated risk index to the data acquired by the performing detection,
wherein the performing weight value determination compares the acquired data and the integrated risk index with an information data reference value and an integrated risk index reference value for updating the weight value,
wherein the performing weight value determination changes a weight value according to the following equation:

$\alpha(n+1)=\alpha(n)$, if $W<d_W$ and $R \geq d_R$ $\alpha(n+1)=\alpha(n)+\delta$, if $W \geq d_W$ $\alpha(n+1)=\alpha(n)-\delta$, if $W<d_W$ and $R<d_R$, where R=integrated risk index,
α=weight value,
α(n+1)=weight value after update,
α(n)=weight value before update,
W=acquired data,
$d_R$=integrated risk index reference value,
$d_W$=information data reference value, and
δ=α(n)/R.
2. The on-vehicle situation detection method of claim 1, wherein the performing driver recognition comprises performing driver data acquisition of acquiring image data of pupils or faces of the current driver through an imaging device, and performing driver identification of comparing the image data of pupils and faces acquired by the performing driver data acquisition with the pre-stored driver information in the memory unit to identify the current driver.
3. The on-vehicle situation detection method of claim 1, wherein in the performing driving pattern calling a pre-stored default driving pattern is called when a driver coinciding with the pre-stored driver information in the performing driver recognition is not present.
4. The on-vehicle situation detection method of claim 1, wherein the performing detection comprises performing driver status detection of detecting one or more of a driver eyelid, a driver pupils, a steering wheel speed, a steering wheel angle, a suspension movement, whether or not an accelerator pedal is operated, whether or not a brake pedal is operated, whether or not a multifunctional switch is operated, whether or not a driver makes conversation, whether or not an Audio Video Navigation (AVN) of the vehicle, is operated, whether or not an air conditioning device is operated, whether or not a gearbox is operated, whether or not a console box is operated, and whether or not a glove box is operated, and performing vehicle surrounding situation detection of detecting a vehicle surrounding situation using one or more of an SCC (Smart Cruise Control), an LKAS (Lane Keeping Assistant System), an SPAS (Smart Parking Assistant System), an AVM (Around View Monitoring), a camera, and a radar.

5. The on-vehicle situation detection method of claim 1, wherein the performing driving pattern learning comprises:
performing driving pattern comparison of comparing the pre-stored driving pattern of the driver called by the performing driving pattern calling with a current driving pattern by the data acquired from the performing detection;
performing driving pattern determination of determining whether difference between the pre-stored driving pattern and the current driving pattern is within a preset noise range;
performing driving pattern storage of learning a current driving pattern when the difference is equal to or less than the preset noise range in the performing driving pattern determination; and
performing noise removal of excluding a current driving pattern from a subject to be learned when the difference exceeds the preset noise range in the performing driving pattern determination.

6. The on-vehicle situation detection method of claim 1, wherein the performing determination comprises selecting from the data acquired from the performing detection a plurality of high-impact data in view of individual datum's impact on the integrated risk index.

7. The on-vehicle situation detection method of claim 6, wherein the performing determination comprises performing calculation of calculating a driver's integrated risk index by adding up respective risk indexes which multiply the selected high-impact data, to which the weight value determined in the performing weigh value determination is assign, by a weight value for each data assigned in the performing weight value determination.

8. The on-vehicle situation detection method of claim 7, wherein the performing determination comprises performing examination of comparing the integrated risk index calculated by the performing calculation with an examination risk index calculated based on the pre-stored driving pattern to determine whether a difference of both indexes is within a preset error range.

9. The on-vehicle situation detection method of claim 8, wherein the performing determination comprises performing control of comparing the integrated risk index with a preset reference risk index when the difference between the integrated risk index and the examination risk index is determined to be within the preset error range in the performing examination, to determine whether or not to provide warning to the current driver.

10. The on-vehicle situation detection method of claim 1, wherein the performing warning comprises:
performing first warning of executing one or more of warning sound generation through a speaker, warning display through an Audio Video Navigation (AVN) or a Head Up Display (HUD) of the vehicle, and vibration notification through vibration of a steering wheel or a seat when an integrated risk index is equal to or greater than a preset first reference risk index and is less than a preset second reference risk index;
performing second warning of holding at least one function of the AVN when the integrated risk index is equal to or greater than the preset second reference risk index and is less than a preset third reference risk index;
performing third warning of forcibly stopping a vehicle when the integrated risk index is equal to or greater than the preset third reference risk index; and
performing information transfer of transferring information for use in the performing weight value determination for an update of the weight value.

* * * * *